United States Patent
Virr et al.

(10) Patent No.: US 9,987,453 B2
(45) Date of Patent: Jun. 5, 2018

(54) HUMIDIFICATION ARRANGEMENT FOR A RESPIRATORY APPARATUS

(71) Applicant: ResMed Limited, Bella Vista, New South Wales (AU)

(72) Inventors: Alexander Virr, Gosford (AU); Donald Darkin, Sydney (AU); Nathan John Row, Sydney (AU); Paul Jan Klasek, Sydney (AU)

(73) Assignee: ResMed Limited, Bella Vista (AU)

( * ) Notice: Subject to any disclaimer, the term of this patent is extended or adjusted under 35 U.S.C. 154(b) by 635 days.

(21) Appl. No.: 14/571,341

(22) Filed: Dec. 16, 2014

(65) Prior Publication Data

US 2015/0101607 A1    Apr. 16, 2015

Related U.S. Application Data

(63) Continuation of application No. 12/449,355, filed as application No. PCT/AU2008/000145 on Feb. 6, 2008, now Pat. No. 8,944,056.

(51) Int. Cl.
*A61M 16/16*   (2006.01)
*A61M 16/10*   (2006.01)
(Continued)

(52) U.S. Cl.
CPC .... *A61M 16/1095* (2014.02); *A61M 16/0003* (2014.02); *A61M 16/0057* (2013.01);
(Continued)

(58) Field of Classification Search
CPC .......... A61M 16/1095; A61M 16/0003; A61M 16/109; A61M 16/142; A61M 16/0057;
(Continued)

(56) References Cited

U.S. PATENT DOCUMENTS 3,865,106 A * 2/1975 Palush ................. A61M 16/08
                                                              128/200.18
3,871,373 A   3/1975 Jackson
(Continued)

FOREIGN PATENT DOCUMENTS

EP     0 672 430      9/1995
JP     11-316035      11/1999
(Continued)

OTHER PUBLICATIONS

International Search Report for PCT/AU2008/00145, dated Feb. 28, 2008.
(Continued)

*Primary Examiner* — Andrew S Lo
(74) *Attorney, Agent, or Firm* — Nixon & Vanderhye P.C.

(57) ABSTRACT

A humidifying apparatus utilizing a semi-permeable membrane portion within a gas conduit where the direction of gas flow within a central lumen is given by an arrow. The humidification apparatus has a helical configuration for the semi-permeable membrane portion, a structural reinforcing member or members, a water channel and a heating element. The helical configuration of an outer wall may be similar to conventional conduits that are in common use in respiratory apparatus. Thus the humidification apparatus may be readily substituted into existing respiratory device by exchanging the gas conduit.

20 Claims, 10 Drawing Sheets

(51) Int. Cl.
*A61M 16/08* (2006.01)
*A61M 16/14* (2006.01)
*A61M 16/00* (2006.01)
*A61M 16/06* (2006.01)

(52) U.S. Cl.
CPC ........ *A61M 16/06* (2013.01); *A61M 16/0875* (2013.01); *A61M 16/109* (2014.02); *A61M 16/1075* (2013.01); *A61M 16/142* (2014.02); *A61M 16/16* (2013.01); *A61M 16/106* (2014.02); *A61M 16/1055* (2013.01); *A61M 16/161* (2014.02); *A61M 16/162* (2013.01); *A61M 2016/003* (2013.01); *A61M 2205/3334* (2013.01); *A61M 2205/3368* (2013.01); *A61M 2206/14* (2013.01)

(58) Field of Classification Search
CPC .............. A61M 16/06; A61M 16/0875; A61M 16/1075; A61M 16/16; A61M 16/106; A61M 16/161; A61M 16/1055; A61M 16/162; A61M 2016/003; A61M 2205/3334; A61M 2205/336; A61M 16/08; A61M 16/0883; A61M 16/14; A61M 16/147; A62B 9/003; F24F 6/02; F24F 6/025; F24F 6/08; F24F 6/10
USPC ............. 128/200.11, 200.24, 201.13, 203.26
See application file for complete search history.

(56) References Cited

U.S. PATENT DOCUMENTS

| | | |
|---|---|---|
| 4,146,597 A | 3/1979 | Eckstein et al. |
| 4,708,831 A | 11/1987 | Elsworth et al. |
| 4,829,997 A | 5/1989 | Douwens et al. |
| 4,861,523 A | 8/1989 | Beran |
| 5,367,604 A | 11/1994 | Murray |
| 5,738,808 A | 4/1998 | Iwamoto |
| 6,010,118 A | 1/2000 | Milewicz |
| 6,078,730 A * | 6/2000 | Huddart ............... A61M 16/08 219/536 |
| 6,201,223 B1 | 3/2001 | Nitta |
| 6,394,084 B1 | 5/2002 | Nitta |
| 6,662,802 B2 | 12/2003 | Smith et al. |
| 6,877,510 B2 | 4/2005 | Nitta |
| 7,469,719 B2 | 12/2008 | Gray |
| 9,327,093 B2 * | 5/2016 | Klasek ............... A61M 16/0875 |
| 2004/0074493 A1 | 4/2004 | Seakins et al. |
| 2009/0320840 A1 | 12/2009 | Klasek et al. |
| 2010/0083965 A1 | 4/2010 | Virr et al. |

FOREIGN PATENT DOCUMENTS

| | | |
|---|---|---|
| WO | WO 97/47348 | 12/1997 |
| WO | WO 2006/069415 | 7/2006 |
| WO | WO 2007/087277 | 8/2007 |

OTHER PUBLICATIONS

International Preliminary Report on Patentability dated Aug. 11, 2009 (6 pages).

* cited by examiner

HUMIDIFICATION ARRANGEMENT FOR A RESPIRATORY APPARATUS

CROSS REFERENCE TO RELATED APPLICATIONS

This application is a continuation of U.S. application Ser. No. 12/449,355, filed Aug. 4, 2009, which is the U.S. national phase of International Application No. PCT/AU2008/000145, filed Feb. 6, 2008, which designated the U.S. and claims priority to AU Application No. 2007900653 filed Feb. 9, 2007, the entire contents of each of which are hereby incorporated by reference.

BACKGROUND OF THE INVENTION

1. Field of the Invention

The present invention relates to humidification arrangements used to control the humidity of breathable gases used in all forms of respiratory apparatus ventilation systems including invasive and non-invasive ventilation, Continuous Positive Airway Pressure (CPAP), Bilevel therapy and treatment for sleep disordered breathing (SDB) conditions such as Obstructive Sleep Apnea (OSA), and for various other respiratory disorders and diseases.

2. Description of the Art

Respiratory apparatus commonly have means to alter the humidity of the breathable gas in order to reduce drying of the patient's airway and consequent patient discomfort and associated complications. The use of a humidifier placed between the positive airway pressure (PAP) device (or flow generator) and the patient mask, produces humidified gas that minimizes drying of the nasal mucosa and increases patient airway comfort.

Many humidifiers types have been proposed, including humidifiers that are either integrated with or configured to be coupled to the relevant respiratory apparatus. While passive humidifiers can provide some relief, generally a heated humidifier is required to provide sufficient humidity and temperature to the air so that patient will be comfortable.

Humidifiers typically comprise a water tub having a capacity of several hundred milliliters, a heating element for heating the water in the tub, a control to enable the level of humidification to be varied, a gas inlet to receive gas from the PAP device, and a gas outlet adapted to be connected to a gas conduit that delivers the humidified pressurized gas to the patient's mask.

However such a humidifier arrangement has a limited area of interaction between the surface of the water in the tub and the gas flowing above so that the capacity to deliver a high absolute humidity rapidly is limited. In addition the humidified air may cool on its path along the conduit from the humidifier to the patient, leading to the phenomenon of "rain-out", or condensation, forming on the inside of the conduit.

Tub-of-water humidifiers are also vulnerable to liquid water spillage if they are not maintained in the vertical. Spillage of liquid water can either travel into the gas conduit to the patient or back into the PAP device and associated electronics or deplete the reservoir of humidifying water. In either of the cases the spillage of water is undesirable.

Several references describe humidification arrangements associated with the gas conduit between the blower or PAP device and the patient mask. These arrangements have consisted of discrete in-line units, tubes of water within the conduit or re-vaporization of water condensate in the gas conduit.

U.S. Pat. No. 4,146,597, U.S. Pat. No. 4,861,523, U.S. Pat. No. 5,367,604 and U.S. Pat. No. 6,010,118 disclose the use of a discrete in-line unit placed somewhere along the gas conduit to the patient. However such discrete humidification units have the disadvantages of being bulky to the patient and impeding the free movement of the gas conduit as the patient moves.

Another humidification scheme is to have a water source enclosed within a tube of a semi-permeable membrane which is then inserted into the gas conduit. The tube may also incorporate heating elements to aid in the generation of water vapour. Examples of such prior art are U.S. Pat. No. 3,871,373, U.S. Pat. No. 4,708,831 and U.S. Pat. No. 6,201,223.

Another example is the use of many tubes that are inserted into the gas conduit, U.S. Pat. No. 4,146,597, U.S. Pat. No. 6,394,084, U.S. Pat. No. 6,557,551 and U.S. Pat. No. 6,877,510. The disadvantage of such arrangements is the impediment to gas flow by the inserted tubes within the gas conduit to the patient. The tubes may also contribute to the cleaning burden within the gas conduit.

U.S. Pat. No. 6,662,802 describes an arrangement for collection of water condensation within the gas conduit and then its re-vaporisation into the gas flow, to reduce the effect of condensation within the gas conduit and to restore the humidity in the gas conduit. However, the apparatus does not have the capacity to increase the absolute humidity beyond what can be gathered as a water source from the condensate in the gas conduit. That is, the arrangement cannot increase the absolute humidity, merely restore it to the absolute humidity at which the gas is supplied to the conduit.

None of these prior art devices provides an entirely satisfactory solution to the provision of humidified breathable gas to the patient, nor to ease of construction and hygiene requirements for a humidification apparatus.

SUMMARY OF THE INVENTION

The present invention aims to provide an alternative humidifier apparatus which overcomes or ameliorates the disadvantages of the prior art, or at least provides a useful choice.

In one form, the invention provides a flexible gas conduit for delivering breathable gas from a PAP device to a patient interface, such as a mask, including a lumen for transport of the breathable gas and a conduit wall including a humidification apparatus.

Preferably, the humidification apparatus comprises a semi-permeable membrane portion which provides a portion of the inner wall between the gas flow within the lumen of the gas conduit and a water channel in the gas conduit. The semi-permeable membrane portion has the characteristic of allowing water vapour to pass through it but not liquid water. Water vapour passing through the semi-permeable membrane portion may then be entrained into the gas flow to the patient interface.

In an alternate form, the humidification apparatus of the invention may comprise a wick and/or capillary action device which is associated with one or more portions of the inner wall of the gas conduit. The wick and/or capillary action device provides water for vaporisation into the gas flow passing through the gas conduit.

A further form of the invention provides a heater which is in thermal contact with the humidification apparatus. The heater may be used to increase the rate of vaporisation of the water within the humidification apparatus.

Optionally, the humidification apparatus and heater may each be divided into one or more separate portions along the gas conduit. The separate portions of each means may be separately controlled.

Further forms of the invention include a method of humidifying breathable gas being supplied to a patient by respiratory apparatus, and the combination of respiratory apparatus with a gas conduit incorporating humidifying apparatus as described herein.

Further forms of the invention are as set out in the appended claims.

BRIEF DESCRIPTION OF THE DRAWINGS

Further preferred embodiments of the invention will now be described with reference to the accompanying drawings, in which.

DETAILED DESCRIPTION OF THE PREFERRED EMBODIMENTS

Figure 1:
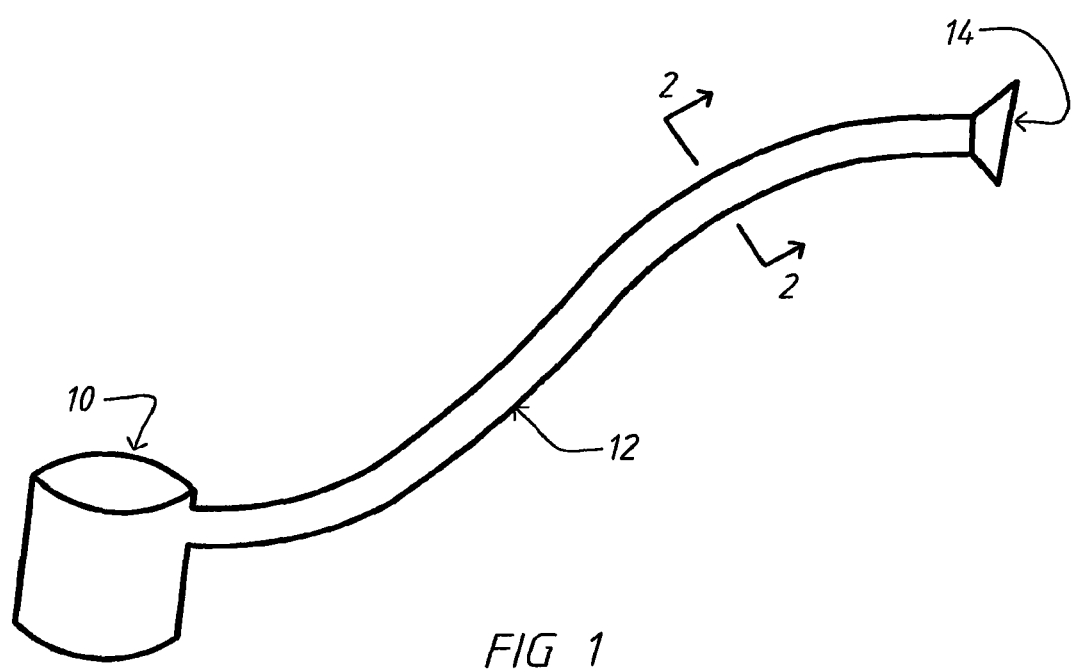
FIG. 1 is a schematic view of the PAP device, gas conduit as the humidifying apparatus and the patient mask, in an embodiment of the present invention.

FIG. 1 schematically shows a PAP device 10 which produces a gas flow and gas pressure that is fed into a flexible conduit 12. The flexible gas conduit 12 has a central lumen 13 (FIG. 2) for conveying the gas flow to the patient mask 14 which is attached to the upper and/or lower airway of the patient or alternatively directly into the patient's airway via a tracheostomy tube. The humidifying apparatus of the present embodiments consists of the gas conduit 12 incorporating a humidification apparatus within it.

Semi-Permeable Membrane Portion

Figure 2:
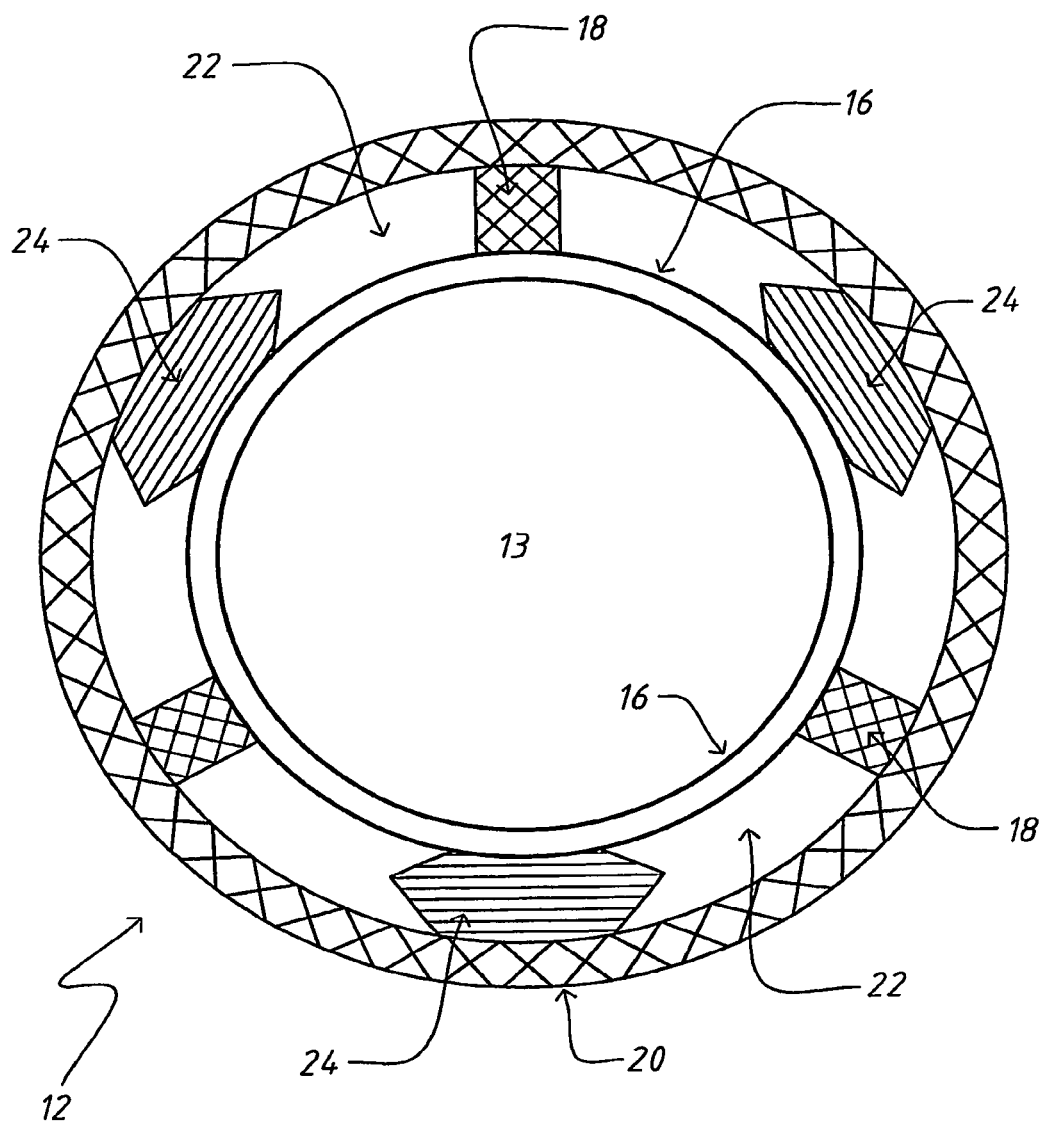
FIG. 2 is an enlarged transverse sectional view taken along the lines 2-2 in FIG. 1, which illustrates an embodiment of the humidification apparatus using water channels.

FIG. 2 illustrates a cross-sectional view of a humidification apparatus within a flexible gas conduit 12, according to a first embodiment. The humidification apparatus may have one or more semi-permeable membrane portions 16 which forms one or more portions of an inner wall of a double-walled conduit 12 and which allows water vapour to pass through the membrane but not liquid water. The inner wall of the double walled conduit 12 may be made entirely of semi permeable membrane portions 16.

The semi-permeable membrane portion may be formed of a material which has fine pores or perforations and may also be hydrophobic, the fineness of the porosity or the perforations and/or the degree of hydrophobic to hydrophilic nature being adapted to result in the desired effect of semi-permeability.

Some examples of semi-permeable membrane materials with suitable characteristics and which are suitably flexible for use in the present invention include:

Porous polytetrafluroethylene (PTFE) materials, microporous PTFE membranes and expanded PTFE (ePTFE) from Gore-tex®, W.I., Gore & Associates, Inc of Maryland USA.

Tyvek® spun polyethylene sheet material from DuPont.

PTFE mesh sold as Fluorcarbon SPECTRA/MESH® by Spectrum Laboratories of Rancho Dominguez, Calif. USA.

Fibrous membranes consisting of auxetic fibres (fibres with a negative Poisson's Ratio).

A more comprehensive discussion of suitable semi-permeable membrane materials is included in Patent Application No. WO 2006/069415 A1 "Respiratory Mask having Gas Washout Vent and Gas Washout Vent Assembly for Respiratory Mask", the contents of which are incorporated herein by reference.

The semi-permeable membrane portion 16 forms the inner wall, adjacent to the central lumen 13, of the flexible gas conduit 12 as shown in FIG. 2.

Figure 3:
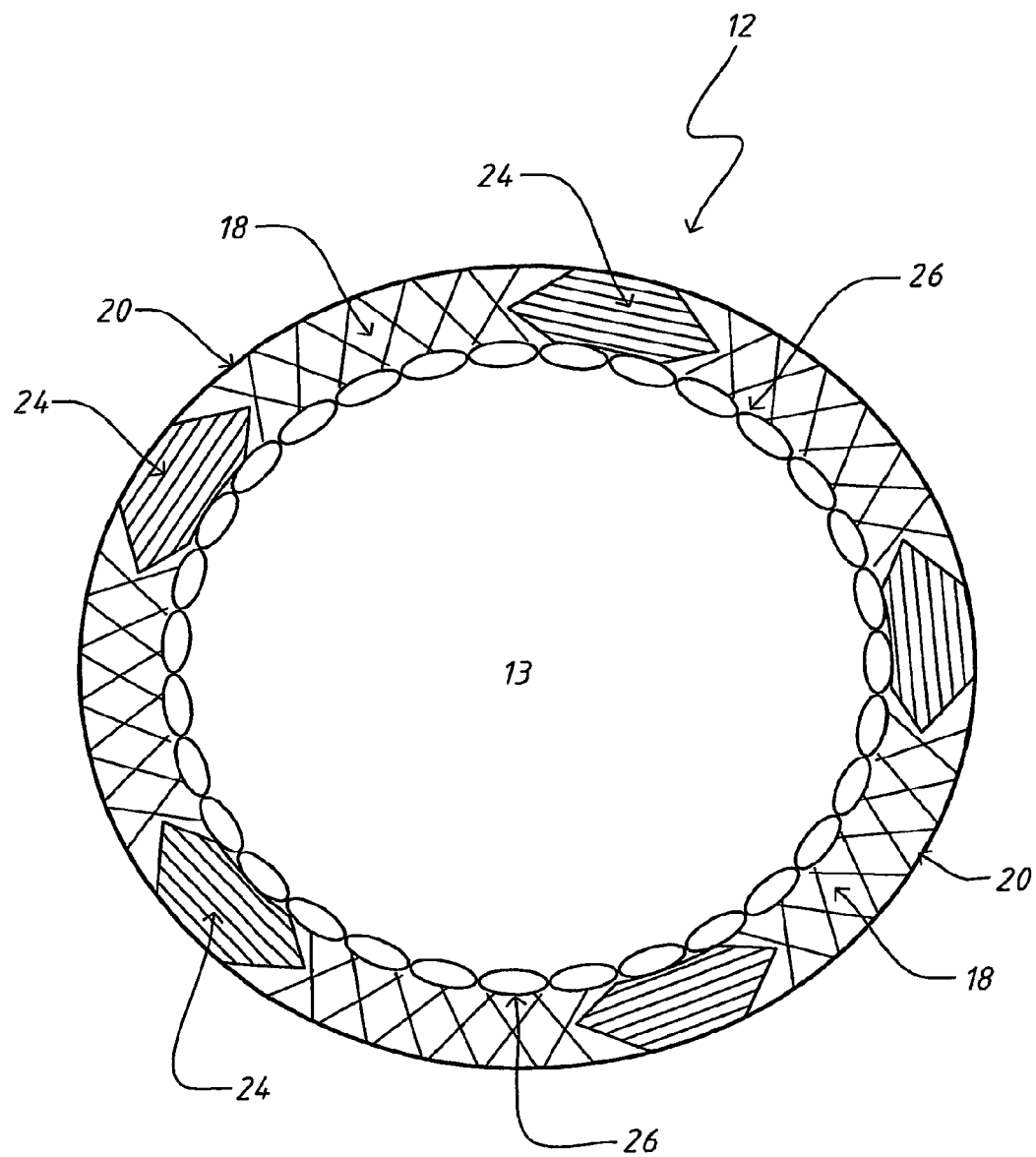
FIG. 3 is an alternative embodiment of FIG. 2 using multiple water tubes to form the inner wall of the gas conduit.
Figure 4:
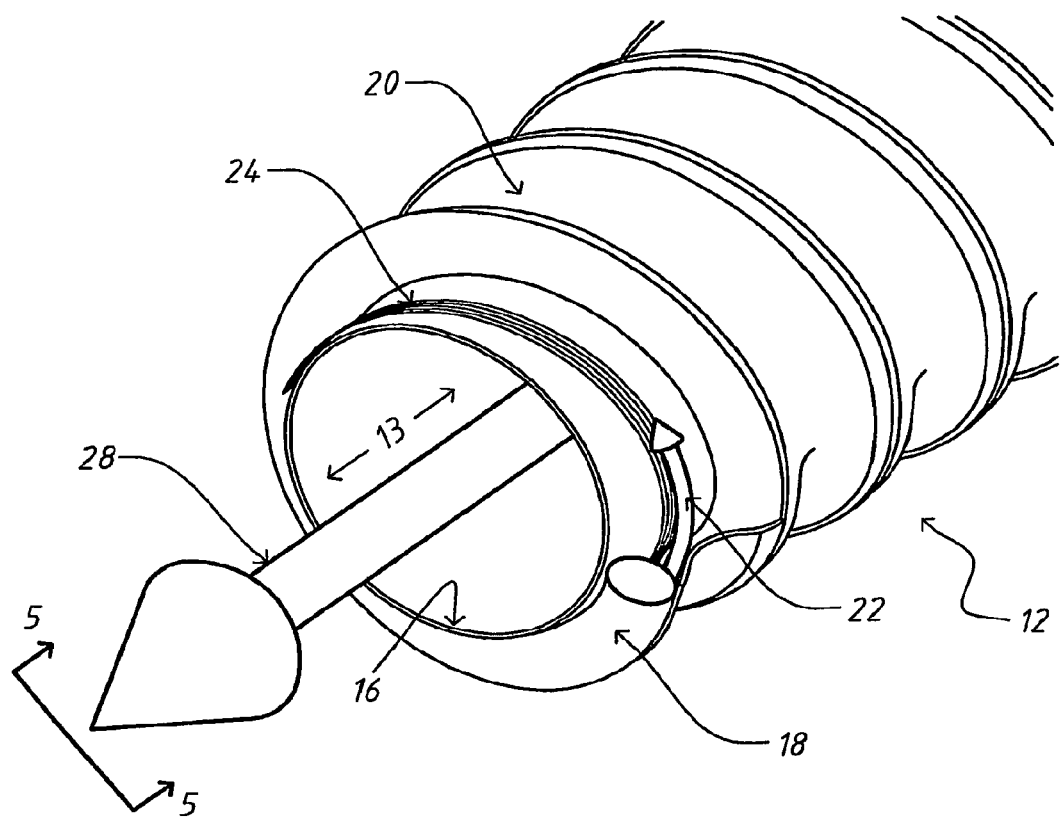
FIG. 4 is an isometric view illustrating an alternative embodiment to FIG. 2.
Figure 5:
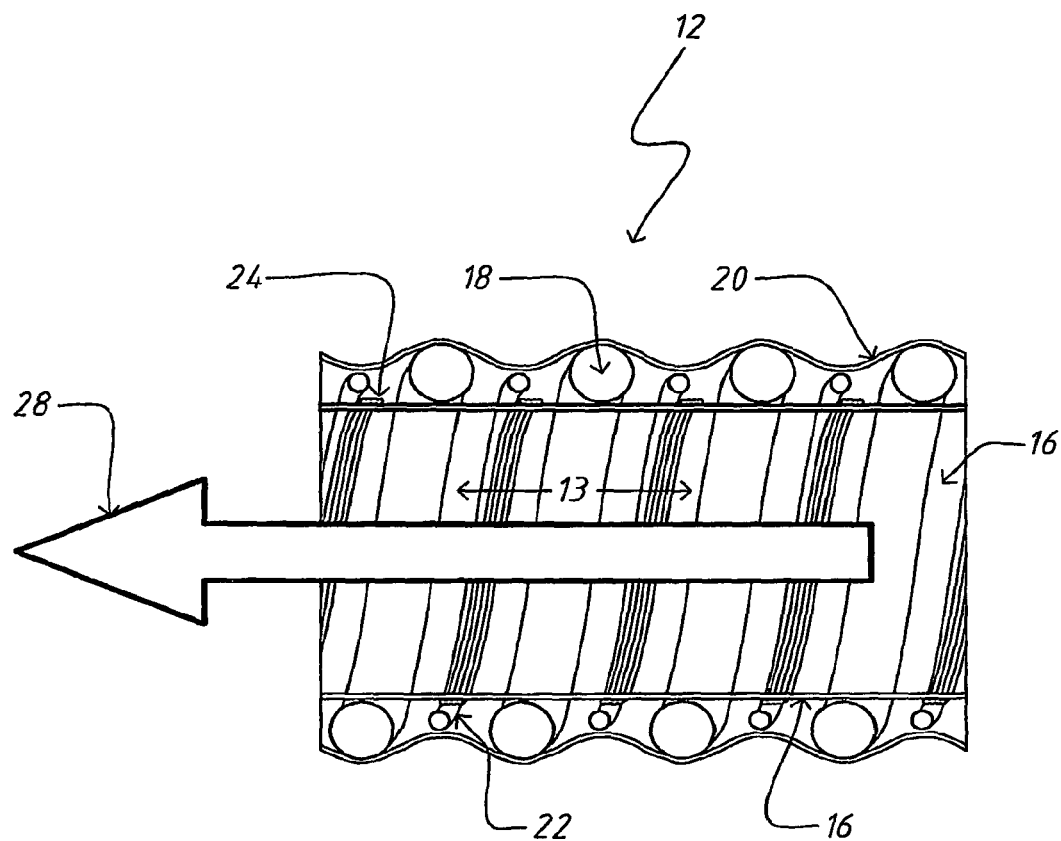
FIG. 5 is longitudinal sectional view taken along the lines 5-5 in FIG. 4.

Structural reinforcing members 18 extend along the wall of the conduit to provide support to the semi-permeable membrane portion 16 and to the outer wall 20 of the gas conduit 12. The reinforcing members 18 also have a spacing function in order that a water channel 22 (or water delivery passage) is formed within the gas conduit 12 between the semi-permeable membrane portion 16 and the outer wall 20. The structural reinforcing members and/or spacers 18 may be longitudinal, as shown in FIGS. 2 and 3, or helical as illustrated in FIGS. 4 and 5 or a combination of these arrangements, but in all the arrangements the reinforcing supports 18 allows the gas conduit 12 to flex to a degree sufficient to allow its use as a flexible gas conduit.

Associated with the water channel 22 there may also be placed one or more heater/s 24 as shown in FIG. 2. The heater 24 is in thermal contact with the water in the water channel 22 and in electrical contact with the electronics associated with the PAP device 10. The heater 24 heats the water in the water channel in order to increase the production of water vapour, which migrates through the semi-permeable membrane portion 16 to mix with the gas flow within the lumen 13 of the gas conduit 12 and thus raise the humidity of the gas travelling through the gas conduit 12.

The heater 24 may consist of a heating element which may for example consist of a resistive conductor. The conductor may consist of multiple resistive conductors connected to each other in series, parallel or segmented along the length of the gas conduit 12 in order to allow uniform, variable and/or sectional heating along the conduit.

Figure 7:
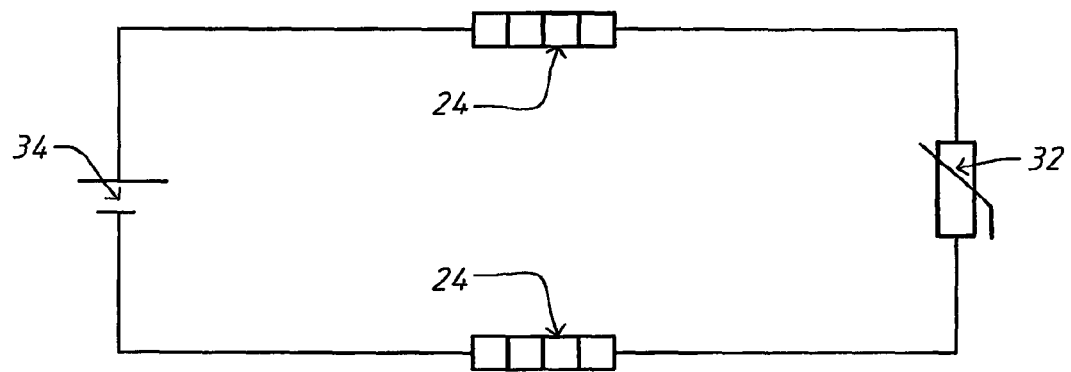
FIG. 7 is a circuit diagram of a heating control circuit employing a PTC thermistor control.

Such a heating element 24 may be controlled by one or more positive temperature coefficient (PTC) thermistors 32 electrically in series with the power supply 34 and the resistive conductors 24, for example as shown in the circuit diagram of FIG. 7. The PTC thermistor 32 operates to decrease heating as the temperature increases towards a desired temperature for the gas flow. The PTC thermistor 32 may be located preferably at the end of the gas conduit 12 towards or at the patient's mask 14, and in one embodiment is located on or incorporated in a cuff of the conduit for connection of the patient interface/mask.

The thermistor 32 may consist of a discrete semiconductor component such as a "bead" thermistor. Alternatively the function of the thermistor 32 may be served by a conductive thermoplastic elastomer (PTC-TPE) with PTC electrical properties. The PTC-TPE can be moulded into a form to fit the patient end of the gas conduit 12 as a cuff portion or a portion of the patient mask 14. Therefore the temperature sensor may be integral to the gas conduit 12 or patient mask 14 or any other associated component.

The heater 24 may be a flexible tape heater as described in the PCT Patent Application No. PCT/AU2007/001715 "Humidifier for a Respiratory Apparatus", the contents of which are incorporated herein by reference.

In one embodiment, the heating element 24 is formed by printed circuit techniques applied to a surface of a flexible substrate such as silicone rubber, all-polyimide or PTFE. Included in the printed circuit techniques which may be used are etched foil, printing and vacuum deposition techniques. The Thermofoil™ range of the type of flexible heaters by Minco of Minneapolis USA, described at www.minco.com, are examples of commercially available strip heaters which may be modified for use in the present application.

Alternatively, the flexible tape heater may be formed as a heating element, for example in the form of a resistive wire or ribbon, laminated between tapes of polycarbonate or other suitable plastics film The outer wall 20 of the gas conduit 12 may provide, protection, insulation and additional structural support to the other elements of the humidifying apparatus but still allows the gas conduit 12 to flex in use.

An alternative embodiment of the humidification apparatus is shown in transverse cross section in FIG. 3. In this embodiment water tubes 26 are formed of semi-permeable membrane portion, for example of the materials discussed above in relation to FIG. 2.

The water tubes 26 are then joined together in a side by side arrangement to form the inner wall of the gas conduit 12. The water tubes 26 may be in a helical or longitudinal or any other suitable configuration to form the inner wall of the gas conduit 12.

The heater 24 is adjacent to the water tubes 26 as shown in FIG. 3, to facilitate heat transfer to the water in the tubes. Water within the water tubes 26 may be heated by the heater 24 to aid in the production of water vapour which migrates through the semi-permeable membrane portion and into the gas flow of the gas conduit 12. The whole arrangement may be encapsulated by an outer wall 20 which may also serve to provide structural support 18 or insulation while still allowing the gas conduit 12 to flex appropriately with patient movement.

FIGS. 4 and 5 illustrate another embodiment of the humidifying apparatus utilising a semi-permeable membrane portion 16 within a gas conduit 12 where the direction of gas flow is given by the arrow 28. This embodiment of the humidification apparatus has a helical configuration for the semi-permeable membrane portion 16, the structural reinforcing member or members 18, the water channel 22 and the heating element 24. The helical configuration of the outer wall 20 may be similar to conventional conduits that are in common use in respiratory apparatus. Thus the humidification apparatus may be readily substituted into existing respiratory device by exchanging the gas conduit 12.

Alternatively it may be possible to insert the gas conduit 12 of the humidification apparatus into an existing conventional conduit of a respiratory apparatus in order to upgrade the humidification performance of a conventional respiratory apparatus.

For the above embodiments, the humidification apparatus may occupy one or more sectors of the circumference of the inner wall of the gas conduit 12. In such a manner the semi-permeable membrane portion 16 then occupies only a portion of the inner wall of the gas conduit 12. In addition the portions of the inner wall formed by the semi-permeable membrane portion 16 may be segmented along the length of the gas conduit 12 inner wall.

The water supply to the water channel 22 or the water tubes 26 in the above embodiments may comprise a single filling at the start of an overnight therapy session of CPAP for OSA, the volume of the water channel 22 or water tubes 26 being a sufficient water supply.

Alternatively a water reservoir (not shown) may be used, which may be an external reservoir or may form part of the gas conduit.

The water reservoir may be located in a portion of the outer wall 20 of the gas conduit 12. The location of the water reservoir along the gas conduit 12 may be at a suitable point along the conduit to allow gravity feed or the use of micro-pump for the water supply.

Alternatively the water reservoir may be located with the PAP device 10 where the connection for the water channels 22 and water tubes 26 to the water reservoir is associated with the connection of the gas conduit 12 to the PAP device 10. The water channels 22 or water tubes 26 may be in a loop arrangement so that water can be circulated through them and back to the water reservoir. Alternatively the water channels 22 or water tubes 26 may individually have an open end for water supply with the other end being closed, but may have a pore or perforation sufficient to allow gas to escape from the water channel 22 or water tube 26 as it fills or draws water.

Wick Embodiment

Figure 6:
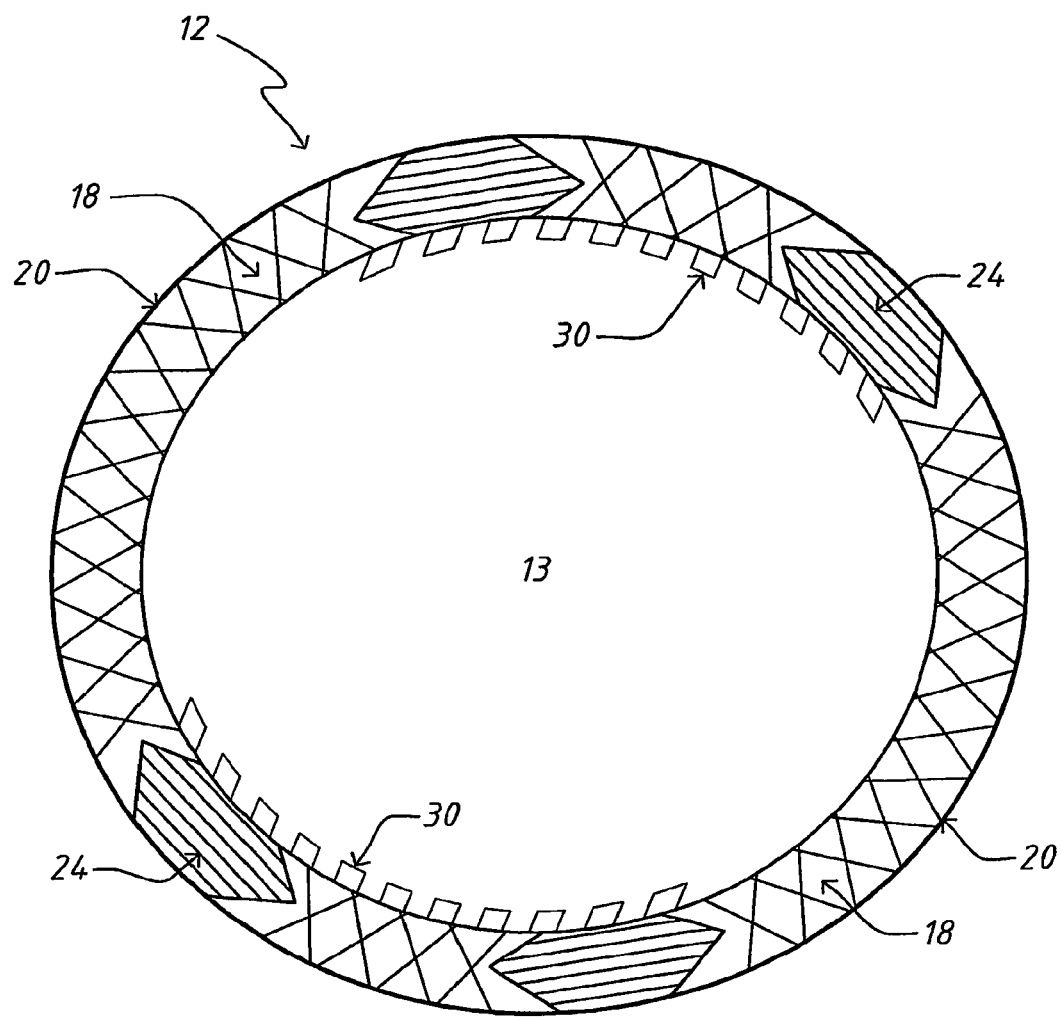
FIG. 6 is an alternative embodiment of FIG. 2, where a wick device is used in the humidification apparatus.

An alternative embodiment for the humidification apparatus is to use a wick and/or capillary action device 30 within the gas conduit 12 as shown in cross-section in FIG. 6. In the following, references to "wick" includes the term "and/or capillary action".

The wick device 30 has the ability to conduct water upon or within the wick device 30 such that water is available for vaporisation into the lumen 13 of the conduit. In addition a capillary action may also be involved within the wick device 30. An example of a suitable wick device 30 is a material which is hydrophilic so that the water has a tendency to spread across the extent of the material. Materials that may be suitable include cotton, activated perfluorinated polymer (e.g. "NAFION" stabilised perfluorosulfonic acid/PTFE copolymer by DuPont), polyester copolymer (e.g. SYMPATEX polyester/polyether copolymer by Sympatex Technologies GmbH of Germany) and polyester fabrics (e.g. COOLMAX polyester fabrics by Invista of USA). Alternatively a material may be imparted hydrophilic characteristics by using a particular liquid film or the application of a gel or solid film.

The wick device 30 may have an internal structural form of a fabric (as shown in FIG. 6), sponge, a film, a bundle of fibres or a hydrophilic porous, flexible solid e.g. plastic, metal or ceramic. The external form of the wick device 30 may be a continuous liner upon the inner wall of the gas conduit 12 or in a strip form that is continuous or in longitudinal segments or a helical arrangement about the inner wall of the gas conduit 12. An alternative embodiment may be the formation of hydrophilic villi (not shown) along the inner wall of the gas conduit 12, such hydrophilic villi serving to increase the area of interaction between the water film upon the hydrophilic villi and the gas in the gas conduit 12.

Alternatively the wick device 30 may be in the form of a very porous membrane that may extend partially or wholly across the transverse cross section of the gas flow path in the gas conduit 12, the material forming the membrane being as per that described above for the wick.

A heater 24 for the wick device 30 may also be present as shown in FIG. 6, having any one of the suitable forms described above.

Alternatively the wick device 30 may be wrapped partially or wholly around a heater 24 that is secured to the inner wall of the gas conduit 12.

The outer wall 20 and reinforcing 18 shown in FIG. 6 serve the functions described above for the semi-permeable membrane portion embodiments in FIGS. 2 to 5.

The water supply for the wick device 30 may be in the forms described above for the semi-permeable membrane portion 16, for example the use of a single fill of water, a water reservoir either as a separate component or co-located with the gas conduit 12 or with the PAP device 10. Alternatively one or more narrow, open-ended pipes, with or without perforations along the pipe length, may be used to supply water from a water reservoir to various locations along the wick device 30.

The wick device 30 has the advantage of self limiting the amount of free liquid water in the gas conduit 12. Free liquid as large droplets or puddles in the gas conduit 12 may be entrained into the gas flow, obstruct the gas conduit 12 or flow back into the PAP device 10. However the wick device 30 only draws as much liquid water as necessary to make a thin film across the wick device 30 and in addition any condensing water may be transferred by the wick device 30 to other areas on the wick or to the water supply.

The wick device 30 embodiment of the humidification apparatus may also be of appropriate transverse cross-sectional dimensions to facilitate its substitution with conventional conduits or insertion into conventional conduits for respiratory apparatus, as described above for the semi-permeable membrane portion 16 humidifying apparatus.

Wick Within Water Channel

Figure 8:
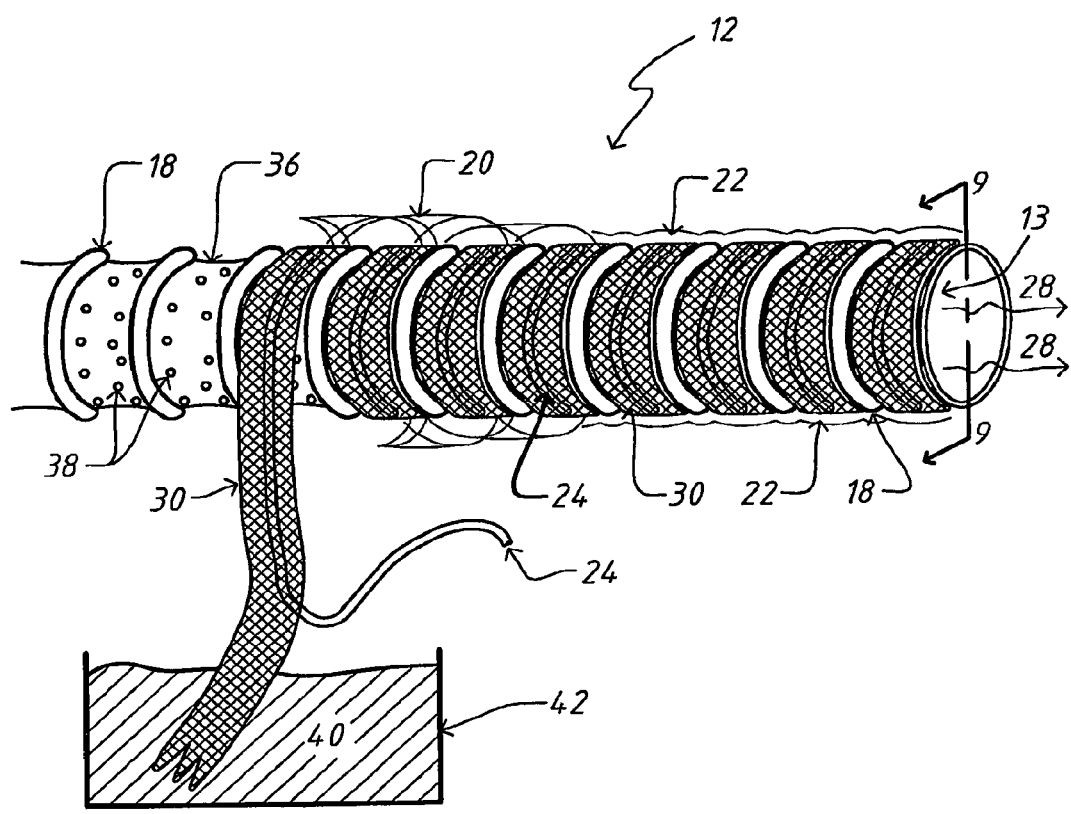
FIG. 8 is a cut-away perspective view of an alternative embodiment of the humidification apparatus where the wick device is located in the water channel.

FIG. 8 schematically shows a cut-away perspective view of an alternative embodiment of the humidification apparatus. A perforated wall 36 forms the inner surface of the gas conduit 12 and is the boundary to the lumen 13. The perforated wall 36 has many through holes 38 that may range in width from 0.2 micro-meters to 1 mm. If the smaller hole 38 sizes are used the perforated wall 36 may act as a semi-permeable membrane which allows the passage of water vapour but not liquid water. About the perforated wall a helical winding of a structural support and spacer 18 is present along the length of the gas conduit 12, in a fashion similar to that described for FIGS. 4 and 5. An outer wall 20 joins the structural support and spacer 18 so that a water channel 22 is formed between the perforated wall 36 and the outer wall 20. The water channel 22 proceeds up the length of the gas conduit 12 in a helical manner in a similar manner to that described for FIGS. 4 and 5.

Within the water channel 22 a wick device 30 is wound about the perforated wall 36 as illustrated in FIG. 8. A heater 24 is also wound about the perforated wall 36, adjacent to and in thermal contact with the wick device 30. Alternatively the wick device 30 may be wrapped around the heater 24 or form a sleeve about the heater 24. The wick device 30 and the heater 24 may be in any one of the forms described above. The wick device 30 draws water 40 from a water reservoir 42 and into the water channel 22. The water is heated in the water channel 22 by the heater 24 to generate vapour 44 (see FIG. 9) that moves through the holes 38 of the perforated wall 36 and into the gas which travels through the lumen 13 in the direction shown by arrows 28.

In an alternative embodiment the structural support and spacer 18 with the wick device 30 and heater 24 may be in a longitudinal arrangement along the gas conduit 12. In yet another embodiment the structural support and spacer 18 may be absent whilst the wick device 30 forms a sleeve over an inner conduit formed by the perforated wall, with the outer wall 20 of the gas conduit enclosing the wick device 30 sleeve and the heater 24.

Figure 9:
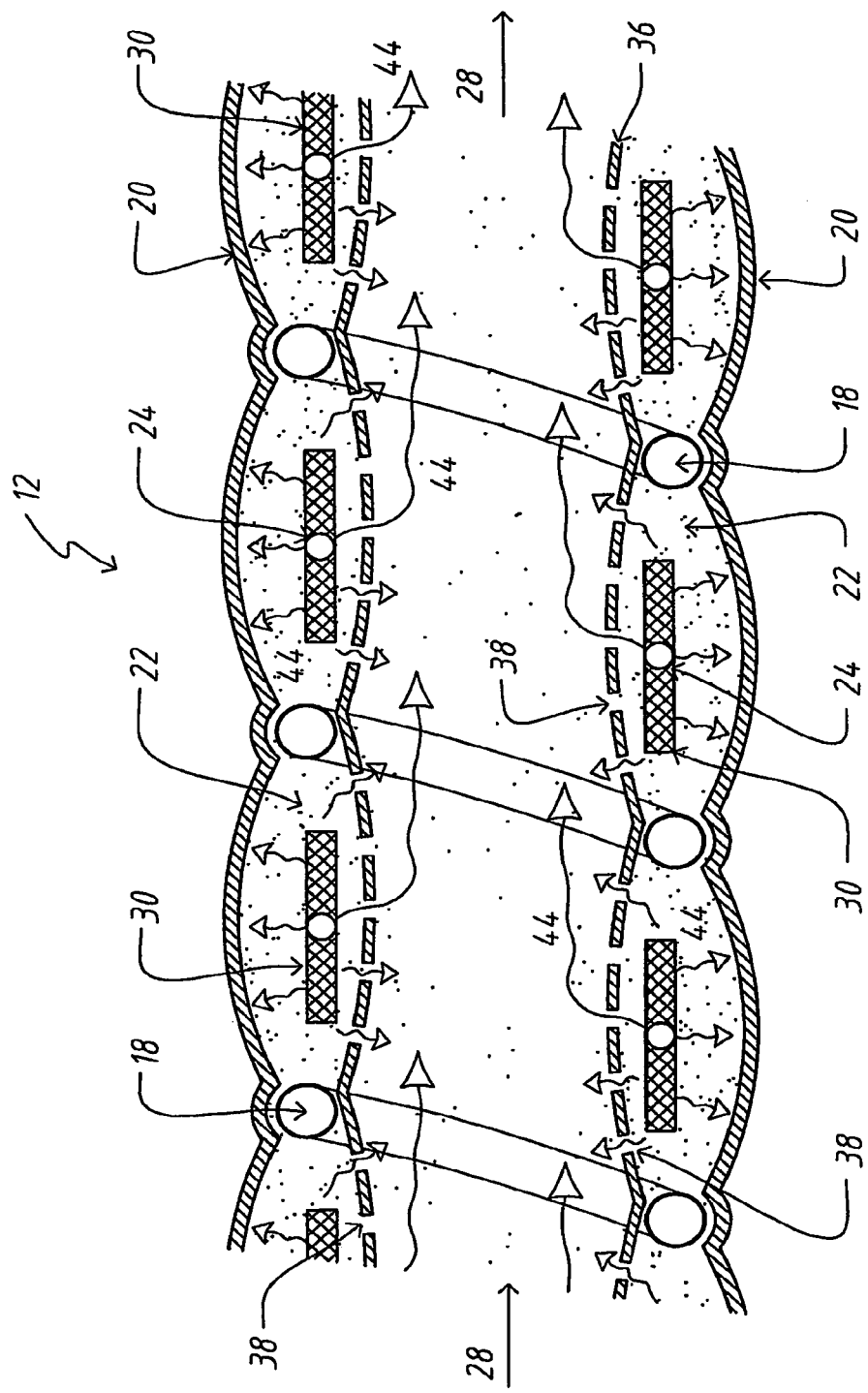
FIG. 9 is a longitudinal cross-sectional view of FIG. 8 along the lines 9-9.

FIG. 9 is a longitudinal cross-sectional view of FIG. 8 along the lines 9-9, schematically illustrating the operation of the humidification apparatus. When the wick device 30 is heated by the heater 24 water vapour 44 evaporates from the liquid water upon and/or within the wick device 30 and into the water channel 22. From the water channel 22 the water vapour 44 moves through the holes 38 of the perforated wall 36 and into the gas which travels through the lumen 13 in the direction shown by the arrows 28. Thus the water channel 22 in this embodiment contains water as a liquid and a substantial amount of water vapour. This is in contrast to the water channel 22 embodiments of FIGS. 2, 4 & 5 where substantially less or no water vapour is present in the water channel 22.

Figure 10:
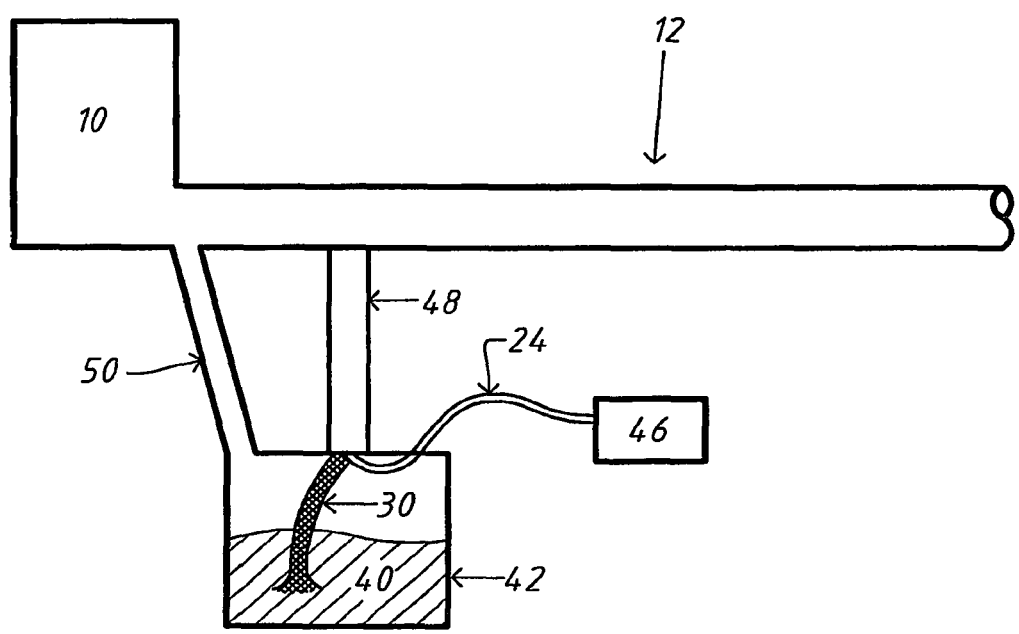
FIG. 10 schematically shows the humidification apparatus of FIG. 8 connected with a PAP device and a cut-away representation of a water reservoir.

FIG. 10 schematically shows the humidification apparatus of the present embodiment connected with the PAP device 10 and a cut-away representation of the water reservoir 42. The humidification apparatus within the gas conduit 12 is connected to the water reservoir 42 and the heater power supply 46 via a water supply pipe 48. The water reservoir 42 is a sealed vessel that is pressurised by a pressurising pipe 50 which is connected to the PAP device 10 and the gas conduit 12. In turn the water channel 22 (FIGS. 8 & 9) is pressurised via the water reservoir 42 through the connecting water supply pipe 48. The gas pressurisation of the water reservoir 42 and the water channel 22 to the same pressure as the gas in the lumen 13 enables the water vapour 44 generated in the water channel 22 to freely migrate and/or diffuse through the perforated wall 36 and into the lumen 13. In an alternative embodiment the pressurising pipe 50 is combined with the water supply pipe 48 such that initial pressurisation of the water channel 22 and water reservoir 42 occurs through the perforated wall 36 from the lumen 13. After initial pressurisation the pressure in the water channel 22 is maintained and exceeded by the heated production of water vapour 44 from the wick device 30 and the heater 24.

In yet an alternative embodiment a device (not shown) for introducing additional gas pressure into the water reservoir 42 is connected to the pressurising pipe 50. The additional gas pressure is used accelerate the water vapour transfer from the water channel 22 to the lumen 13, since there will be a continuous gas flow from the water channel 22 into the lumen 13.

Additional Use of the Semi-Permeable Membrane

An alternate embodiment of all the embodiments of the humidification apparatus described above includes the use of a semi-permeable membrane across the transverse cross-section of lumen 13. Preferably the transverse semi-permeable membrane (not shown) would be located close to the patient mask 14, but may be located at another or multiple locations along the gas conduit 12. The purpose of the transverse semi-permeable membrane is to prevent the passage of water droplets along the gas conduit 12 to the patient.

Another alternate embodiment of all the embodiments of the humidification apparatus that use a semi-permeable membrane as described above, includes the use of a semi-permeable membrane that has multiple layers (not shown). The layers of semi-permeable membranes differ in their ability to repel liquid water (hydrophobicity), structural strength and ability to retain the precipitates of dissolved ions in the liquid water, for example Calcium Carbonates and various other precipitates commonly found in mineralised or "hard water". The first semi-permeable membrane layer adjacent the liquid water may have the least hydrophobicity but the greatest ability to retain the precipitates as they are deposited in the process of water vaporisation through the semi-permeable membrane layers. Consequently the first semi-permeable membrane also has the greatest structural strength so that it does not fail with the accumulation of precipitates. Successive semi-permeable membrane layers have increasing hydrophobic properties with reducing structural strength. Thus the semi-permeable membrane layers act as a graded filter as well as a graded barrier to liquid water.

In another embodiment the multiple layer semi-permeable membrane may also be used across the transverse cross-section of lumen 13 as described above. However in this embodiment the multiple layer semi-permeable membrane may also function as a graded filter for mucous and the like which may be introduced into the gas conduit 12 when the patient exhales.

The humidification apparatus embodiments described above do not suffer from the problem of tilting and consequential spillage of water that a conventional tub humidifier is prone to. This is because the liquid water is enclosed as in the case of the semi-permeable membrane portion 16 or the liquid water is only present as a thin film as in the case of the wick device 30.

Segmentation of Humidification and Heating along the Gas Conduit

The humidification apparatus has been described above with its humidification apparatus 16, 30 and heater 24 segmented in location along the gas conduit 12. The segmentation may be in the form of multiple separate segments of the humidification apparatus 16, 30 and/or with the heater 24. Such an embodiment may produce humidity in one more segments of the gas conduit 12, then in one or more other segments of the gas conduit 12 the condensate could be collected and then re-vaporised with the heater 24.

The segmentation of the humidification apparatus 16, 30 and the heater 24 may also be in time of operation for each segment of the humidification apparatus. For example humidification may be timed to the patient's inspiration, such that sufficient water vapour is delivered into the passing gas stream during inspiration to maintain a desired humidity. The level of humidity in the gas conduit may be regulated by the use of a humidity sensor (not shown) and a gas flow sensor (not shown) to detect inspiration. The output of these sensors is then used to control the level of heating with the heater and/or the supply of water to the humidification apparatus. The humidity sensor may be located where-ever convenient along the gas conduit 12, most preferably at some distance from the patient end of the gas conduit. The gas flow sensor may be located within the PAP device 10, gas conduit 12 or the patient mask 14. The gas flow sensor may consist of a temperature sensor located near the patient end of the gas conduit 12 or in the patient mask 14. In such positions the patient's respiration cycle of inspiration to respiration may be sensed by changes in the sensed temperature.

Another example of timed operation of the humidification apparatus 16, 30 and heater 24 is at a cold start-up in cold climates where it is desirable to provide warm air to the patient firstly and then humidified warm air. For a cold start-up: initially the humidification apparatus in the conduit may not have water supplied to it so that when the heater starts there is no energy intensive heating of water and consequently the heating of the gas flow is rapid. Once the desired gas temperature is obtained water is then supplied to the humidification apparatus to begin humidification before the onset of adverse respiratory symptoms associated with the breathing of low humidity air. The water may also be supplied at a slower controlled rate at the beginning of the humidification.

Disposable

The materials and construction of all the above embodiments may be of a cost and construction to make them disposable. Or in an alternative embodiment the wick device 30 may be a removable liner and/or an insert that may be replaced in the gas conduit 12.

Sterility

Sterilisation may be provided within the humidification apparatus to counteract the growth and lodgement of disease causing agents within the humidification apparatus. In one embodiment, this may include a method and device to produce a sterilising temperature within the humidifying apparatus, for example through the heater 24 described above. An alternative sterilisation may be by the use of a chemical treatment of one or more surfaces or materials within the apparatus, for example the wick or semi-permeable membrane portion may be permanently impregnated with a chemical that inactivates viruses and arrests bacterial growth. Alternatively a sterilising fluid may be supplied to the humidification apparatus 16, 30 instead of water, for a short period when the humidification apparatus is not connected to the patient.

In another embodiment the semi-permeable membrane 16 and/or the perforated wall 36 may have a pore size less than 0.2 micrometers sufficiently small to prevent the passage of viruses and bacteria from the water within the water channel 22 or water tubes 26 to the gas within the lumen 13. Alternatively the semi-permeable membrane 16 or the perforated wall 36 may have an adjacent membrane layer which performs the function of preventing the passage of viruses and bacteria whilst allowing the free passage of water vapour.

In a further embodiment a sterile filter (not shown) may used across the transverse cross-section of lumen 13. The sterile filter prevents the passage of viruses and bacteria but allows the passage of gas and water vapour through the lumen 13. The sterile filter may be placed across the lumen 13 at the patient mask 14 end of the humidification apparatus or any other convenient location across the lumen 13.

In another embodiment the gas conduit 12 may contain an ultraviolet light device (not shown) within a portion of the length of the gas conduit 12. The ultraviolet light device illuminates all the gas and water vapour within the lumen 13 and is of sufficient intensity and appropriate wavelength to inactivate all bacteria and viruses within the lumen 13. The ultraviolet light device portion of the gas conduit 12 may be located at the patient mask 14 end of the humidification apparatus.

Gas Conduit Internal Wall Projections

For the above embodiments the internal wall of the gas conduit 12 may have projections (not shown) extending into the lumen 13. These projections may serve to facilitate the turbulent mixing of the gas stream with the water vapour issued from the humidification apparatus 16, 30 and hence promote faster humidification of the gas stream. Alternatively the projections may also contain extensions of the humidification apparatus 16, 30. These projections may facilitate the transfer of the water vapour from the humidification apparatus 16, 30 located at the slow boundary layer of the gas flow at the wall of lumen 13, to the faster and more turbulent gas flow in the body of the lumen 13.

The humidification apparatus embodiments described above have the advantage of presenting a large area of interaction between the gas flow stream and the water compared to that for a conventional water tub humidifiers. In addition the present humidification apparatus invention is compact and incorporated unobtrusively within the gas conduit 12 to the patient. The gas conduit 12 may have a flexibility which is comparable to that of a conventional conduit in the prior art. In addition there is minimal impedient to the gas flow or to the desirable acoustic monitoring from the patient mask 14 through the gas conduit 12

Although the invention has been herein shown and described in what is conceived to be the most practical and preferred embodiments, it is recognized that departures can be made within the scope of the invention, which is not to be limited to the details described herein but is to be accorded the full scope of the appended claims so as to embrace any and all equivalent assemblies, devices and apparatus.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise, comprised and comprises where they appear.

It will further be understood that any reference herein to known prior art does not, unless the contrary indication appears, constitute an admission that such prior art is commonly known by those skilled in the art to which the invention relates.

The invention claimed is:

1. A humidifier configured to humidify and convey a flow of respiratory gas, the humidifier being in the form of a flexible, tubular conduit and comprising:
    a central lumen that is part of the conduit and has an open first end and an open second end, the central lumen being configured to convey the flow of respiratory gas to a patient's airways;
    a liquid water retainer that is part of the conduit and is configured to retain liquid water, the liquid water retainer being located outside any flow of respiratory gas; and
    a heater that is part of the conduit and is configured to heat the liquid water in the liquid water retainer to generate water vapor.

2. A respiratory apparatus configured to provide positive pressure gas to a patient's airways, the respiratory apparatus comprising:
    a positive airway pressure device configured to generate a flow of positive pressure gas;
    a patient interface configured to engage the patient's face and be in communication with the patient's airways; and
    the humidifier according to claim 1, the humidifier being configured to convey the flow of positive pressure gas to the patient interface.

3. A humidifier in the form of a flexible, tubular conduit and comprising:
    a first portion that is part of the conduit and is configured to convey gas through the humidifier, the first portion comprising a central lumen with an open first end and an open second end;
    a second portion that is part of the conduit and surrounds the first portion and positioned to be outside a flow of any gas conveyed through the humidifier, the second portion comprising a liquid water retainer and a heater configured to vaporize liquid water retained within the liquid water retainer; and
    a flexible outer wall housing the first and second portions.

4. The humidifier according to claim 3, wherein the central lumen is defined by a flexible, gas permeable inner wall configured to facilitate a flow of water vapour from the liquid water retainer to the central lumen.

5. The humidifier according to claim 4, wherein the gas permeable inner wall is configured to prevent a flow of liquid water from the liquid water retainer to the central lumen.

6. The humidifier according to claim 3, wherein the heater is positioned inside the liquid water retainer and comprises a plurality of heating elements extending along a length of the liquid water retainer.

7. The humidifier according to claim 6, wherein the plurality of heating elements define a plurality of channels configured to receive a flow of water from a water inlet.

8. The humidifier according to claim 3, wherein the liquid water retainer comprises a plurality of water tubes forming one or more portions of a flexible, gas permeable inner wall defining the central lumen.

9. The humidifier according to claim 3, wherein the liquid water retainer comprises a wick and/or a capillary action device.

10. A respiratory apparatus configured to provide positive pressure gas to a patient's airways, the respiratory apparatus comprising:
    a positive airway pressure device configured to generate a flow of positive pressure gas;
    a patient interface configured to engage the patient's face and be in communication with the patient's airways; and
    the humidifier according to claim 3, the humidifier being configured to convey the flow of positive pressure gas to the patient interface.

11. The respiratory apparatus according to claim 10, wherein the positive airway pressure device comprises a liquid water reservoir configured to supply water to the liquid water retainer.

12. The respiratory apparatus according to claim 11, wherein the liquid water reservoir and the liquid water retainer are configured to be in a loop arrangement so that liquid water is circulated between the liquid water retainer and the liquid water reservoir.

13. A humidifier configured to humidify and convey a flow of respiratory gas, the humidifier being in the form of a flexible, tubular conduit and comprising:
    an air inlet, an air outlet and a central lumen that is part of the conduit and extends from the air inlet to the air outlet, the central lumen being configured to convey the flow of respiratory gas to a patient's airways;
    a liquid water retainer that is part of the conduit and is configured to retain liquid water, the liquid water retainer having a closed first end and a closed second end, a liquid water inlet being located at the second end; and a heater that is part of the conduit and is configured to heat the liquid water in the liquid water retainer to generate water vapor.

14. The humidifier according to claim 13, wherein the central lumen is defined by a flexible, gas permeable inner wall configured to facilitate a flow of water vapour from the liquid water retainer to the central lumen.

15. The humidifier according to claim 14, wherein the gas permeable inner wall is configured to prevent a flow of liquid water from the liquid water retainer to the central lumen.

16. The humidifier according to claim 13, wherein the heater is positioned inside the liquid water retainer and comprises a plurality of heating elements extending along a length of the liquid water retainer.

17. The humidifier according to claim 16, wherein the plurality of heating elements define a plurality of channels configured to receive a flow of water from the liquid water inlet.

18. A respiratory apparatus configured to provide positive pressure gas to a patient's airways, the respiratory apparatus comprising:

a positive airway pressure device configured to generate a flow of positive pressure gas;

a patient interface configured to engage the patient's face and be in communication with the patient's airways; and the humidifier according to claim 13, the humidifier being configured to convey the flow of positive pressure gas to the patient interface.

19. The respiratory apparatus according to claim 18, wherein the positive airway pressure device comprises a liquid water reservoir configured to be connected to the liquid water inlet and supply water to the liquid water retainer.

20. The respiratory apparatus according to claim 19, wherein the liquid water reservoir and the liquid water retainer are configured to be in a loop arrangement so that liquid water is circulated between the liquid water retainer and the liquid water reservoir.

* * * * *